United States Patent [19]

Clausen et al.

[11] Patent Number: 4,606,698
[45] Date of Patent: * Aug. 19, 1986

[54] CENTRIFUGAL BLOOD PUMP WITH TAPERED SHAFT SEAL

[75] Inventors: Earl W. Clausen, Wayzata; Lloyd C. Hubbard, Minnetonka, both of Minn.

[73] Assignee: MICI Limited Partnership IV, Minneapolis, Minn.

[*] Notice: The portion of the term of this patent subsequent to May 20, 2003 has been disclaimed.

[21] Appl. No.: 628,727

[22] Filed: Jul. 9, 1984

[51] Int. Cl.⁴ .................. F04D 29/12; F16J 15/38
[52] U.S. Cl. .................. 415/170 A; 415/173 R; 415/174; 277/92; 277/169; 277/165
[58] Field of Search .......... 415/170 A, 170 R, 171, 415/172 R, 173 R, 173 A, 174, 206; 277/165, 169, 92, 95

[56] References Cited

U.S. PATENT DOCUMENTS

| | | | |
|---|---|---|---|
| Re. 28,742 | 3/1976 | Rafferty et al. | 415/90 |
| 851,457 | 4/1907 | Verner | 416/183 |
| 874,431 | 12/1907 | Pitkin | 415/97 |
| 1,225,805 | 5/1917 | Griepe | 415/87 |
| 1,880,911 | 10/1932 | Durdin, Jr. | 415/174 |
| 2,154,199 | 4/1939 | Colwell et al. | 415/170 A |
| 2,231,690 | 2/1941 | Sheldrick et al. | 415/174 |
| 2,243,227 | 5/1941 | Stratton | 415/170 A |
| 2,465,625 | 3/1949 | Aue | 415/99 |
| 2,471,753 | 5/1949 | Johnston | 417/420 |
| 2,481,172 | 9/1949 | Staggs | 417/420 |
| 2,540,968 | 2/1951 | Thomas | 384/537 |
| 2,668,068 | 2/1954 | Bredemeier | 415/170 A |
| 2,669,668 | 2/1954 | Okulitch et al. | 310/104 |
| 2,686,747 | 8/1954 | Wurtz et al. | 415/170 A |
| 2,810,349 | 10/1957 | Zozulin | 417/420 |
| 3,299,819 | 1/1967 | McCoy | 417/420 |
| 3,366,068 | 1/1968 | Rye | 415/173 A |
| 3,541,607 | 11/1970 | Greene | 415/112 |
| 3,608,088 | 9/1976 | Dorman et al. | 3/1 |
| 3,647,324 | 3/1972 | Rafferty et al. | 417/420 |
| 3,652,176 | 3/1972 | Walsh | 415/9 |
| 3,676,015 | 7/1972 | Hodgman, Jr. | 415/202 |
| 3,702,745 | 11/1972 | Segebrecht | 415/170 A |
| 3,864,055 | 2/1975 | Kletschka et al. | 415/1 |
| 3,901,623 | 8/1975 | Grennan | 415/141 |
| 3,957,389 | 5/1976 | Rafferty et al. | 415/1 |
| 3,970,408 | 7/1976 | Rafferty et al. | 415/60 |
| 4,037,984 | 7/1977 | Rafferty et al. | 415/60 |
| 4,135,253 | 1/1979 | Reich et al. | 3/1 |
| 4,185,617 | 1/1980 | Hutchins | 128/1 |
| 4,257,744 | 3/1981 | Watson | 416/244 |
| 4,304,532 | 12/1981 | McCoy | 417/420 |
| 4,344,723 | 8/1982 | Ellingson | 406/53 |
| 4,380,416 | 4/1983 | Menager | 415/174 |
| 4,408,952 | 10/1983 | Schweinfurter | 415/53 |

FOREIGN PATENT DOCUMENTS

| | | | |
|---|---|---|---|
| 1810943 | 5/1970 | Fed. Rep. of Germany | 415/170 A |
| 0159371 | 6/1957 | Sweden | 415/170 A |

*Primary Examiner*—Robert E. Garrett
*Assistant Examiner*—H. Edward Li
*Attorney, Agent, or Firm*—Kinney & Lange

[57] ABSTRACT

A centrifugal blood pump has a tapered seal between a pump housing wall and a hub of an impeller which provides a fluid tight seal interface surrounding a drive shaft which is connected to the impeller and which extends through the pump housing wall. The tapered seal has a maximum radial dimension adjacent to the wall and a minimum radial dimension adjacent the hub so that air bubbles (which seek the smallest shaft diameter) will not insulate the seal interface edges from fluid flow. The seal interface, which is perpendicular to the drive shaft axis, is located in a high flow area between the wall and the hub to increase cooling effects.

28 Claims, 8 Drawing Figures

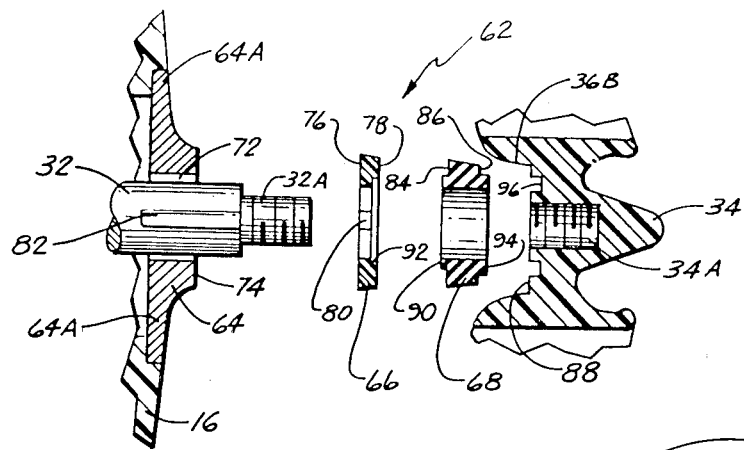
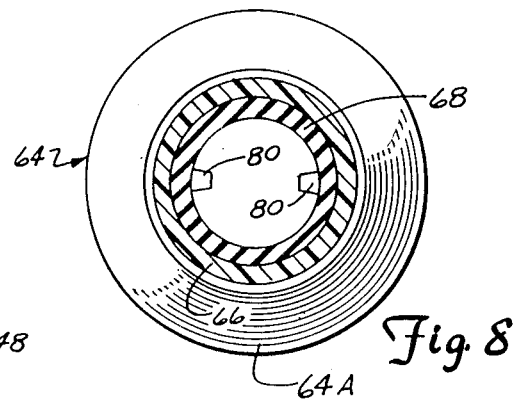
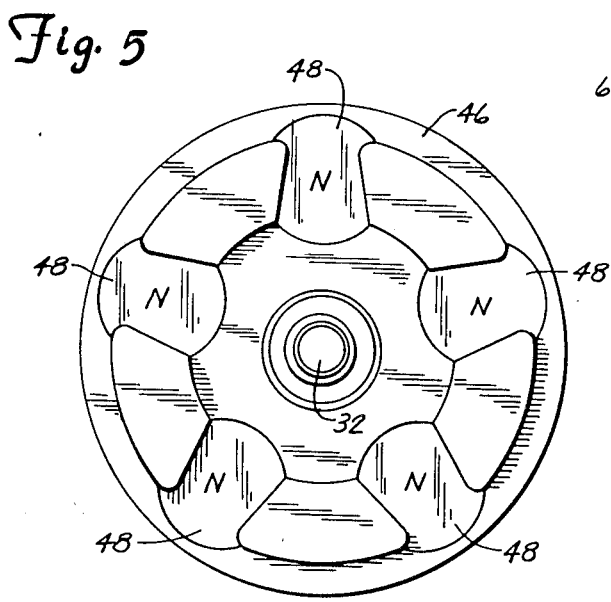
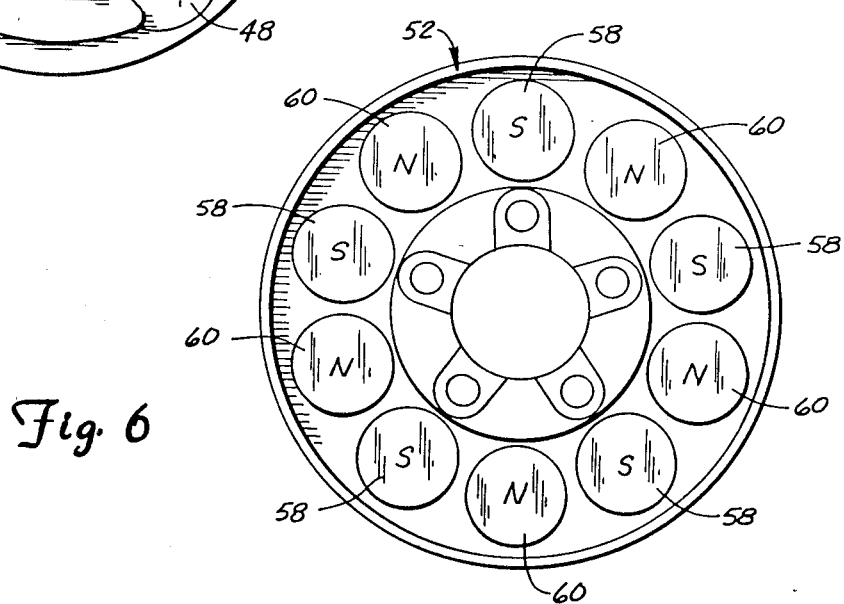

CENTRIFUGAL BLOOD PUMP WITH TAPERED SHAFT SEAL

REFERENCE TO COPENDING APPLICATION

Reference is made to our copending application filed on even date entitled "Centrifugal Blood Pump with Impeller".

BACKGROUND OF THE INVENTION

1. Field of the Invention.

The present invention is related to centrifugal blood pumps.

2. Description of the Prior Art.

Centrifugal pumps have been used for many years to pump a wide variety of different fluid materials. In general, a centrifugal pump includes a pumping chamber with an inlet aligned with a rotational axis of the pump, an outlet adjacent the periphery of the pumping chamber, and an impeller mounted within the pumping chamber for rotation about the axis. The impeller in such pumps can be mounted on a drive shaft which extends outside the pumping chamber to a rotational drive source or the shaft can be mounted within the pumping chamber as a spindle about which the impeller rotates (rotatably driven by means other than the rotation of the shaft, such as a magnetic drive arrangement). In any case, as the impeller is rotated, it imparts centrifugal force and velocity to the fluid, thus pumping the fluid from the pump inlet to the pump outlet.

In recent years, centrifugal pumps have been used extensively for pumping blood during open heart surgery. Examples of centrifugal blood pumps are shown in the following U.S. patents: Rafferty et al No. Re. 28,742; Dorman et al No. 3,608,088; Rafferty et al No. 3,647,324; Kletschka et al No. 3,864,055; Rafferty et al No. 3,957,389; Rafferty et al No. 3,970,408; Rafferty et al No. 4,037,984; and Reich et al No. 4,135,253.

The pumping of blood requires great care to avoid any damage to the red corpuscles, or any of the other constituents of blood. Any practical blood pump useful as part of heart/lung bypass equipment during open heart surgery must deliver the requisite flow volumes under pressure, without damaging the blood being pumped.

In a centrifugal pump, and in particular in a centrifugal pump for pumping liquids such as blood, a fluid tight seal between the rotating part (e.g. the drive shaft) and the non-rotating part (e.g. the housing) is an important factor in the performance of the pump. Friction at the seal produces heat which can damage both the components of the pump and the blood being pumped if not dissipated.

In prior art centrifugal pumps, the rotation of the impeller can lead to generation of an air bubble surrounding the shaft. This air bubble tends to seek the smallest shaft diameter, which is adjacent the shaft seal. In prior art centrifugal pumps, the area adjacent the shaft seal has also been a relatively stagnant or low flow area in terms of fluid flow within the pumping chamber. The air bubble tends to insulate the seal from the flow of the fluid within the pump chamber, thus decreasing the dissipation of heat generated by fricton at the seal interface.

SUMMARY OF THE INVENTION

The present invention is an improved centrifugal blood pump which has a tapered seal between the pump housing wall and the hub of the impeller for providing a fluid tight seal interface which surrounds the shaft at an intermediate position between the wall and the hub. This tapered seal has a maximum radial dimension adjacent the wall and a minimum radial dimension adjacent the hub.

With the pump of the present invention, the seal is tapered so that air bubbles (which seek the smallest shaft diameter) will not insulate the seal interface edges from fluid flow. In addition, the seal interface is located in a high flow area between the wall and the hub to increase cooling.

In preferred embodiments, the tapered seal includes a seal stator which is connected to the wall, a seal rotor which is rotatable with the impeller and movable axially on the shaft, and a resilient ring positioned between the hub and the seal rotor. The seal stator surrounds the shaft and defines a first seal face which is generally tranverse to the axis and which is located at an intermediate position between the wall and the hub. The seal rotor is positioned coaxially on the shaft and defines a second seal face which faces the first seal face and which is generally transverse to the axis. The resilient ring urges the second seal face into engagement with the first seal face to provide the fluid tight seal interface around the shaft.

BRIEF DESCRIPTION OF THE DRAWINGS

FIG. 5 is a view of the rotor along view 5—5 of FIG. 3.

FIG. 6 is a view of the drive plate along view 6—6 of FIG. 3.

FIG. 7 is an exploded view, partially in section, of the tapered shaft seal of the centrifugal pump.

FIG. 8 is a sectional view of the shaft seal along section 8—8 of FIG. 3.

DETAILED DESCRIPTION OF THE PREFERRED EMBODIMENTS

Figure 1:
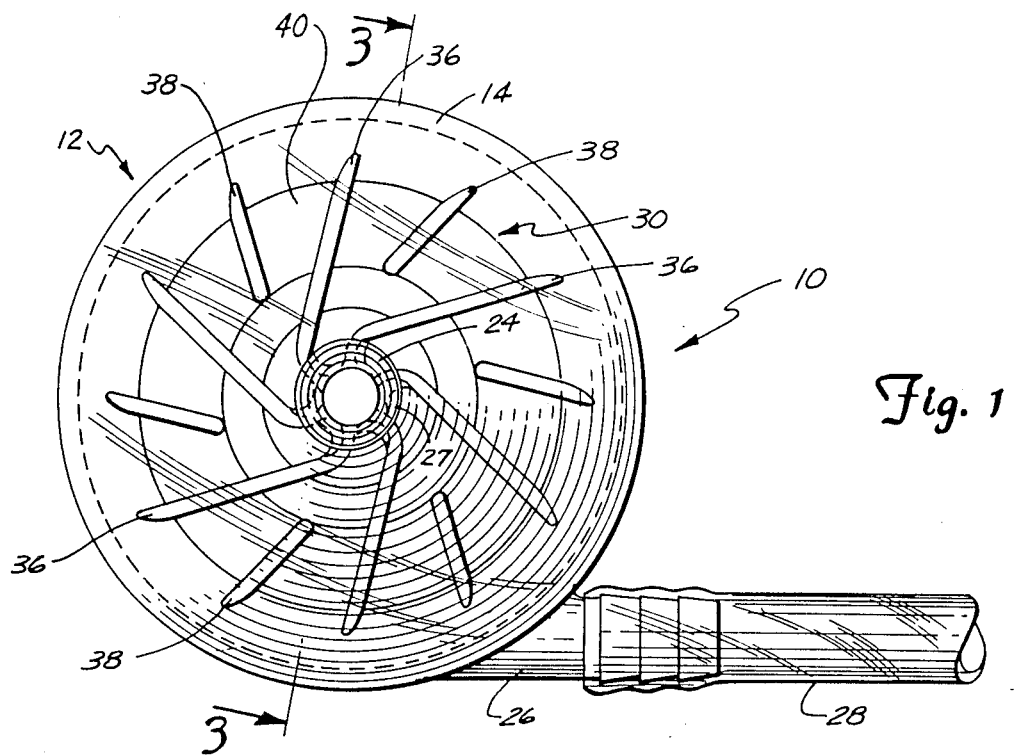
FIG. 1 is a front view of the centrifugal pump of the present invention.
Figure 2:
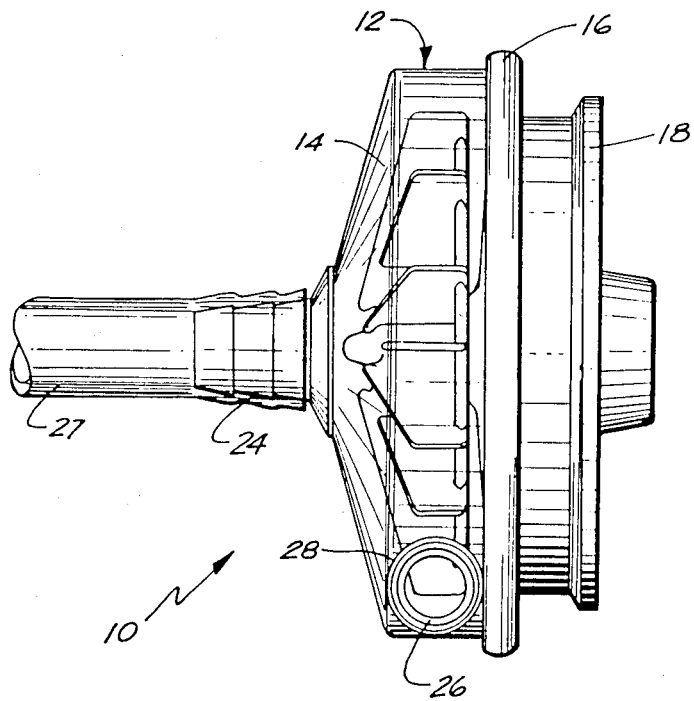
FIG. 2 is a side view of the centrifugal pump.

In the preferred embodiment shown in the Figures, centrifugal pump 10 of the present invention includes a three-part housing 12 formed by front housing section 14, center wall housing section 16, and rear housing section 18. Front and center sections 14 and 16 are sealed to define pumping chamber 20. Center and rear sections 16 and 18 are sealed to define rotor chamber 22.

Front housing section 14 (which is preferably transparent so that operation of the pump can be visually monitored) includes axially aligned pump inlet 24 and tangential pump outlet 26. Blood or other biological fluid is received at inlet 24 from inlet tubing 27 and is pumped to outlet 26 and outlet tubing 28 by rotation of impeller 30 within pumping chamber 20.

Impeller 30 is mounted on a threaded outer end 32A of shaft 32, and is rotated about an axis defined by shaft 32. Impeller 30 includes a conical shaped impeller hub 34 (with internal threads 34A for engaging threaded outer end 32A), a plurality of long blades 36, a plurality of short blades 38, and circular flange 40.

Long blades 36 are attached at their inner ends to impeller hub 38. Flange 40 is attached to and is supported by long blades 36. Short blades 38 are supported by flange 40. In the particular embodiment shown in the Figures, long and short blades 36 and 38 are alternately spaced about the circumference of impeller 30.

Large diameter impellers require a greater number of blades in order to achieve pumping efficiency. By use of short blades 38 supported by flange 40, impeller 30 achieves pumping efficiency while retaining a small hub diameter, since only long blades 36 are attached to hub 34.

Shaft 32 is mounted for rotation by a pair of axially aligned ball bearings 42 and 44. Ball bearing 42 is press fitted into center wall section 16, while ball bearing 44 is press fitted into rear housing section 18.

Figure 3:
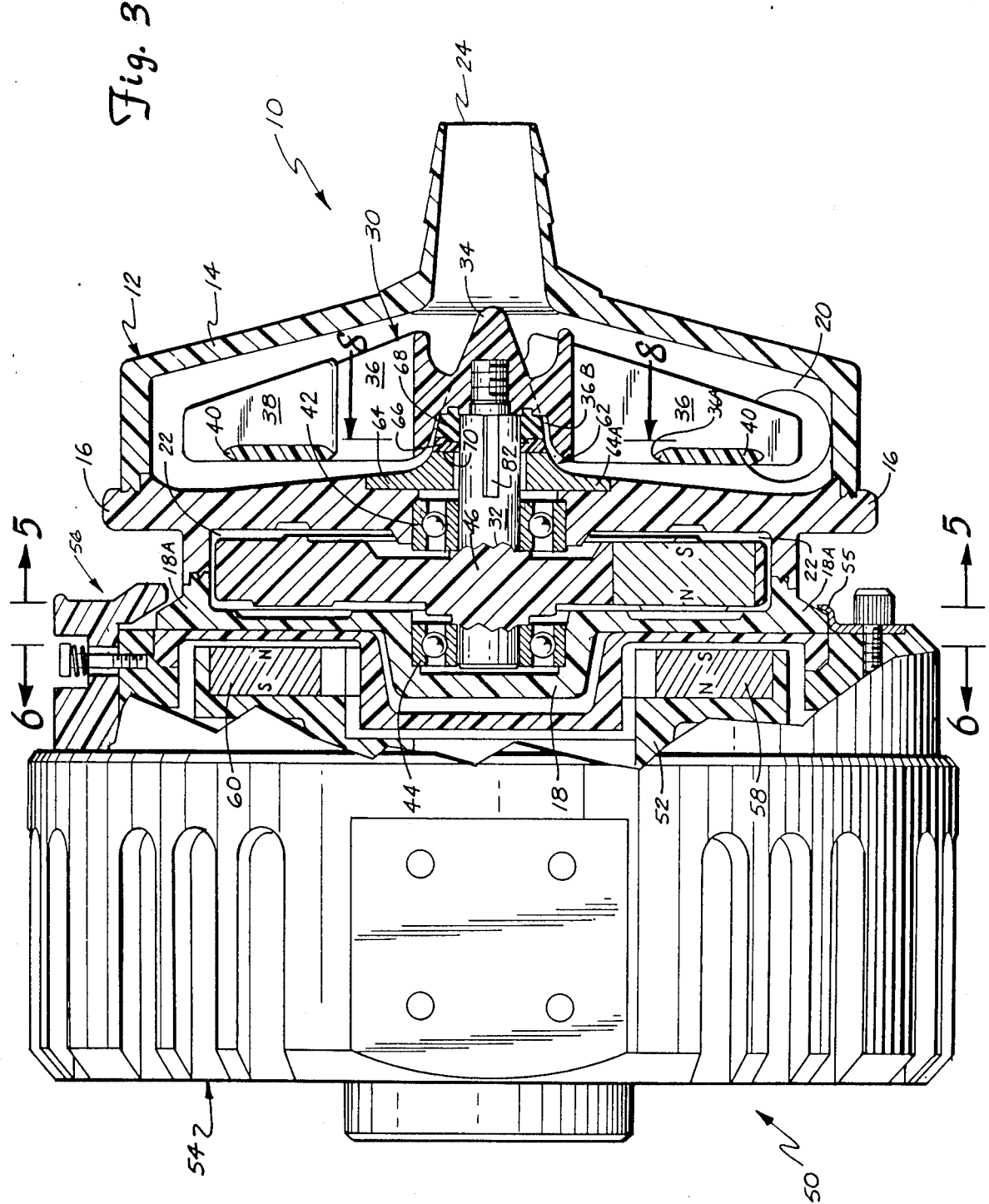
FIG. 3 is a sectional view of the centrifugal pump along section 3—3 of FIG. 1.
Figure 4:
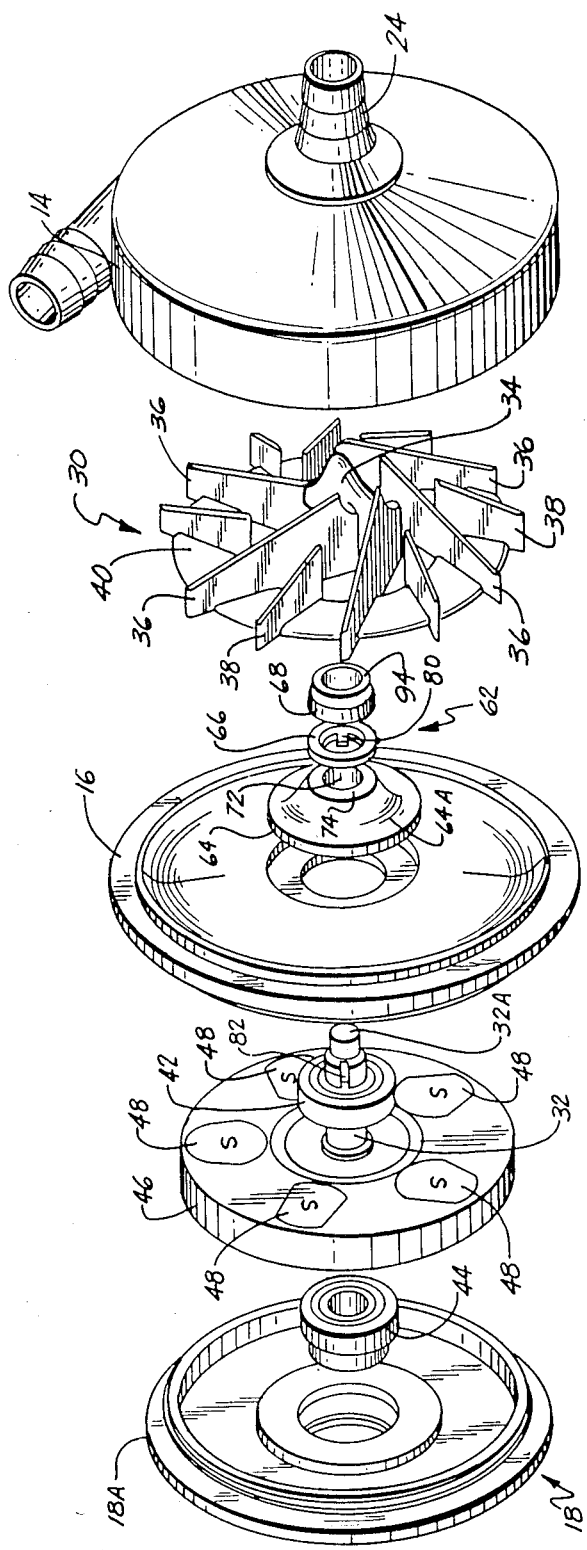
FIG. 4 is an exploded perspective view of the centrifugal pump.

Rotor 46 is connected to shaft 32, so that as rotor 46 rotates within rotor chamber 22, shaft 32 and impeller 30 are rotated. In the particular embodiment shown in the Figures, pump 10 is a magnetically driven pump. Rotor 46 carries a plurality of small magnets 48. Each magnet 48 has the same pole orientation (which in the particular embodiment shown has the north (N) pole closest to drive console 50). Magnets 48 are equally spaced around the circumference of rotor 46 and, in the particular embodiment shown in FIG. 3, five magnets 48 spaced at 72° intervals (center-to-center) from one another are carried by rotor 46.

Drive console 50 includes drive plate 52 which is rotated by motor 54 about an axis which is aligned with the axis of shaft 32. Clip 55 and spring-loaded latch 56 engage flange 18A of rear housing section 18 to hold pump housing 12 in position adjacent drive console 50. Pump housing 12 can be quickly removed from engagement with drive console 50 by lifting latch 56.

Drive plate 52 carries five equally spaced south (S) pole magnets 58 and five equally spaced north (N) pole magnets 60. Magnets 58 and 60 are arranged alternately (as shown in FIG. 6). This gives both attractive and repelling force to magnets 48 carried by rotor 46. This magnetic drive allows the use of small, discrete magnets in pump 10, rather than a single large magnet with multiple poles. This provides a significant cost reduction which is of particular advantage since pump housing 12, when used for pumping blood or other biological fluids, must be disposed of or resterilized after a single use.

In the present invention, leakage of fluid from pumping chamber 20 into rotor chamber 22 is prevented by a tapered shaft seal 62 formed by seal stator 64, seal rotor 66, and resilient elastomer spring 68. Tapered seal 62 is tapered to conform to the taper of impeller hub 34 so that an air bubble (which seeks the smallest shaft diameter within pumping chamber 20) will not insulate the seal interface edges from fluid flow. Tapered seal 62 provides a seal interface 70 between seal stator 64 and seal rotor 66 which is generally perpendicular to the axis of shaft 32 and which is located at an intermediate position between wall 16 and hub 34. The location of the seal interface 70 is in a high fluid flow area, which increases cooling effects and improves dissipation of heat caused by friction at seal interface 70.

In the preferred embodiment of the present invention shown in FIG. 1, seal stator 64 is fixed to center wall section 16, seal stator 64 is a high thermal conductivity material (such as nickel-plated aluminum or anodized aluminum). Seal stator 64 has a central passage 72 which is axially aligned with shaft 32 and is of sufficient diameter so that shaft 32 does not contact seal stator 64. Front face 74 of seal stator 64 defines the location of seal interface 70 and is, in the preferred embodiment shown generally perpendicular to the axis of shaft 32.

Seal stator 64 has a flange 64A at its rear end which extends outward in a radial direction and generally conforms to the surface of wall 16 at the rear end of pumping chamber 20. Flange 64B provides a large surface area for seal stator 64, thus increasing the ability of seal stator 64 to transfer heat generated at seal interface 70.

Seal rotor 66 is positioned on shaft 32 adjacent seal stator 64. Rear face 76 of seal stator 66 engages front face 74 of seal stator 64 to provide seal interface 70. Front face 78 of seal rotor 66 faces and is engaged by spring 68. Seal rotor 66 has a pair of inwardly projecting keys 80 which engage axially extending keyways 82 on shaft 32 so that seal rotor 66 can move in the axial direction and yet rotates with shaft 32. Such a keyed arrangement may not be necessary if, by friction fit or bonding, the seal rotor 66 is driven by the spring 68 to rotate therewith. In a preferred embodiment, seal rotor 66 is a low friction polymer material such as nylon.

Spring 68 is an elastomer (such as silicone rubber) ring which is mounted coaxially on shaft 32 between impeller hub 34 and seal rotor 66. Rear face 84 of spring 68 engages front face 78 of seal rotor 66, and front face 86 of spring 68 engages rear face 88 of hub 34. Elastomer spring 68 is maintained under compression by hub 34, which is threaded on outer end 32A of shaft 32, so that it urges seal rotor 66 in an axial direction into engagement with seal stator 64. Spring 68 preferably has an annular rib 90 which is positioned in annular groove 92 in front face 78 of seal rotor 66 and has an annular rib 94 which is positioned in annular groove 96 in the rear face 88 of hub 34. Ribs 90 and 94 help to maintain an axial alignment of spring 68 so that an essentially uniform axial force is applied to seal rotor 66. In another embodiment (not shown), the resilient elastomer spring is positioned between the seal stator and wall section with which it is mounted (rather than between the seal rotor and hub) and the seal rotor is fixed to the hub to effectuate the sealing of the pumping chamber about the shaft.

To increase fluid flow in the area of seal interface 70, each of the long blades 36 of impeller 30 has a rear edge 36A which is closer to center wall 16 than are impeller hub 34 and seal interface 70. Each long blade 36 has an inner edge 36B which extends from rear edge 36A to impeller hub 34, and which is closely spaced and generally parallel to the outer surface of tapered seal 62.

Although the present invention has been described with reference to preferred embodiments, workers skilled in the art will recognize that changes may be made in form and detail without departing from the spirit and scope of the invention. For example, although the particular embodiment of pump 10 shown in the Figures utilizes a synchronous magnetic drive, the shaft seal is equally applicable to pumps in which other forms of coupling (including direct coupling) between shaft 32 of pump 10 and motor 54 of console 50 are provided. In addition, where the shaft is a fixed spindle about which the impeller is rotated by other means (such as a magnetic drive arrangement wherein magnets are mounted directly on the impeller), the shaft seal of the present invention seals the pumping chamber from the bearings and lubricants between the shaft and impeller hub.

What is claimed is:

1. A centrifugal pump for pumping a biological fluid such as blood, the pump comprising:
   a pump housing having a pumping chamber therein and having an inlet and an outlet connected to the pumping chamber;
   a shaft extending in an axial direction into the pump housing to define a rotational axis;
   an impeller for rotation about the rotational axis within the pumping chamber, the impeller having a hub; and
   a tapered seal between a wall of the pump housing and the hub for providing a fluid-tight seal interface surrounding the shaft at an intermediate position between the wall and the hub, the tapered seal having a maximum radial dimension adjacent the wall and a minimum radial dimension adjacent the hub; wherein an outer surface of the tapered seal and an outer surface of the hub form an essentially continuous tapered outer surface so that the seal interface is located in a high fluid flow area within the housing and trapped air within the biological fluid will not tend to accumulate adjacent the seal interface.

2. The centrifugal pump of claim 1 wherein the seal interface is generally transverse to the axial direction.

3. The centrifugal pump of claim 2 wherein the tapered seal comprises:
   a seal stator connected to the wall and surrounding the shaft, the seal stator defining a first seal face which is generally transverse to the axial direction and is located intermediate the wall and the hub;
   a seal rotor positioned coaxially on the shaft between the seal stator and the hub, the seal rotor defining a second seal face which faces the first seal face and which is generally transverse to the axial direction, the seal rotor being mounted for rotation with the impeller and being movable in the axial direction; and
   a resilient ring positioned coaxially on the drive shaft for urging the first and second seal faces into engagement to provide the fluid-tight seal interface around the shaft.

4. The centrifugal pump of claim 3 wherein the seal stator has a radially outward extending flange at an end closest to the wall.

5. The centrifugal pump of claim 3 wherein the seal stator is metal.

6. The centrifugal pump of claim 5 wherein the seal stator is aluminum.

7. The centrifugal pump of claim 3 wherein the seal rotor is a low friction polymer ring.

8. The centrifugal pump of claim 7 wherein the low friction polymer is a nylon material.

9. The centrifugal pump of claim 3 wherein the resilient ring is an elastomer spring ring.

10. The centrifugal pump of claim 9 wherein the elastomer is a silicone rubber.

11. The centrifugal pump of claim 3 wherein the resilient ring is positioned between the hub and the seal rotor for urging the seal rotor toward the seal stator.

12. The centrifugal pump of claim 11 wherein the seal rotor has an annular groove in a surface facing the resilient ring, and wherein the resilient ring has an annular rib which engages the annular groove in the seal rotor.

13. The centrifugal pump of claim 11 wherein the hub has an annular groove in a surface facing the resilient ring, and wherein the resilient ring has an annular rib which engages the annular groove in the hub.

14. The centrifugal pump of claim 1 wherein the impeller hub has a generally conical shape with a maximum diameter adjacent the tapered seal.

15. The centrifugal pump of claim 1 wherein the shaft is a drive shaft which extends through the wall with a first end within the pumping chamber and a second end on an opposite side of the wall from the pumping chamber; and wherein the hub is attached to the first end of the drive shaft.

16. A centrifugal pump for pumping a biological fluid such as blood, the pump comprising:
   a pump housing having a pumping chamber therein and having an inlet and an outlet connected to the chamber;
   a shaft extending in an axial direction into the pump housing to define a rotational axis;
   an impeller for rotation about the rotational axis within the pumping chamber, the impeller having a hub;
   a seal stator connected to a wall of the pump housing surrounding the shaft, the seal stator defining a first seal face which is generally transverse to the axial direction and is located at an intermediate position between and spaced apart from the wall and the hub;
   a seal rotor positioned coaxially on the shaft between the first seal face and the hub, the seal rotor defining a second seal face which faces the first seal face and which is generally transverse to the axial direction, the seal rotor being mounted for rotation with the impeller and being movable in the axial direction; and
   spring means for urging the first and second seal faces into engagement to provide a fluid tight seal around the shaft at a seal interface which is of greater diameter than the hub so that trapped air within the biological fluid will not tend to accumulate adjacent the seal interface; wherein the seal stator, the seal rotor, the spring means, and the impeller hub form a generally conical extension from the wall into the pumping chamber, the conical extension having an essentially continuous outer surface with a maximum diameter adjacent the wall and a minimum diameter at an end of the impeller hub furthest from the wall, so that the seal interface defined by the first and second seal faces is in an area of high fluid flow.

17. The centrifugal pump of claim 16 wherein the seal stator has a radially outward extending flange at an end closest to the wall.

18. The centrifugal pump of claim 17 wherein the seal stator is tapered with a maximum radial dimension adjacent the wall and a minimum radial dimension at the first seal face.

19. The centrifugal pump of claim 16 wherein the seal stator is metal.

20. The centrifugal pump of claim 19 wherein the seal stator is aluminum.

21. The centrifugal pump of claim 16 wherein the seal rotor is a low friction polymer ring.

22. The centrifugal pump of claim 21 wherein the low friction polymer is a nylon material.

23. The centrifugal pump of claim 16 wherein the spring means is an elastomer ring which surrounds the drive shaft and is maintained under compression to urge the first and second seal faces into engagement.

24. The centrifugal pump of claim 23 wherein the elastomer is silicon rubber.

25. The centrifugal pump of claim 23 wherein the elastomer ring is positioned between the hub and the seal rotor for urging the seal rotor toward the seal stator.

26. The centrifugal pump of claim 25 wherein the seal rotor has an annular groove in a surface facing the elastomer ring, and wherein the elastomer ring has an annular rib which engages the annular groove in the seal rotor.

27. The centrifugal pump of claim 25 wherein the hub has an annular groove in a surface facing the elastomer ring, and wherein the elastomer ring has an annular rib which engages the annular groove in the hub.

28. The centrifugal pump of claim 16 wherein the shaft is a drive shaft which extends through the wall with a first end within the pumping chamber and a second end on an opposite side of the wall from the pumping chamber; and wherein the hub is attached to the first end of the drive shaft.

* * * * *